United States Patent [19]
Columbus et al.

[11] Patent Number: 5,743,861
[45] Date of Patent: Apr. 28, 1998

[54] BLOOD COLLECTION DEVICE

[75] Inventors: Richard L. Columbus, Rochester; Harvey J. Palmer, Lima, both of N.Y.; John Brian Barclay, Winthrop Harbor, Ill.; Ted J. Hanagan, Libertyville, Ill.; Michael G. Lowery, Wildwood, Ill.; Edward J. Gutierrez, Gurnee, Ill.; Douglas Duroux Hansmann, Libertyville, Ill.; Daniel Patrick Schmidt, Oak Creek, Wis.

[73] Assignee: Abbott Laboratories, Abbott Park, Ill.

[21] Appl. No.: 589,916

[22] Filed: Jan. 23, 1996

[51] Int. Cl.⁶ .................................................. A61B 5/00
[52] U.S. Cl. .................................................. 600/577
[58] Field of Search ........................ 128/760, 762–765, 128/770; 604/317, 403, 411, 415

[56]     References Cited

U.S. PATENT DOCUMENTS

| | | |
|---|---|---|
| 3,382,865 | 5/1968 | Worrall, Jr. . |
| 3,405,706 | 10/1968 | Cinqualbre . |
| 3,604,410 | 9/1971 | Whitacre . |
| 3,696,806 | 10/1972 | Sausse . |
| 3,848,579 | 11/1974 | Villa-Real . |
| 4,150,089 | 4/1979 | Linet ................................ 422/102 |
| 4,166,450 | 9/1979 | Abramson ......................... 128/764 |
| 4,212,308 | 7/1980 | Percarpio ......................... 128/766 |
| 4,676,256 | 6/1987 | Golden ............................. 128/762 |
| 5,033,476 | 7/1991 | Kasai ............................... 128/764 |
| 5,097,842 | 3/1992 | Bonn ................................ 128/762 |
| 5,179,960 | 1/1993 | Sarrine ............................. 128/764 |
| 5,314,412 | 5/1994 | Rex .................................. 128/762 |

FOREIGN PATENT DOCUMENTS 3941105   12/1989   Germany .

*Primary Examiner*—Max Hindenburg
*Attorney, Agent, or Firm*—David L. Weinstein

[57]     ABSTRACT

Disclosed is a fluid collection device wherein multiple, individual, samples of fluid can be withdrawn simultaneously. The device includes an evacuated chamber and an adapter which substantially simultaneously distributes the blood to each individual chamber.

13 Claims, 11 Drawing Sheets

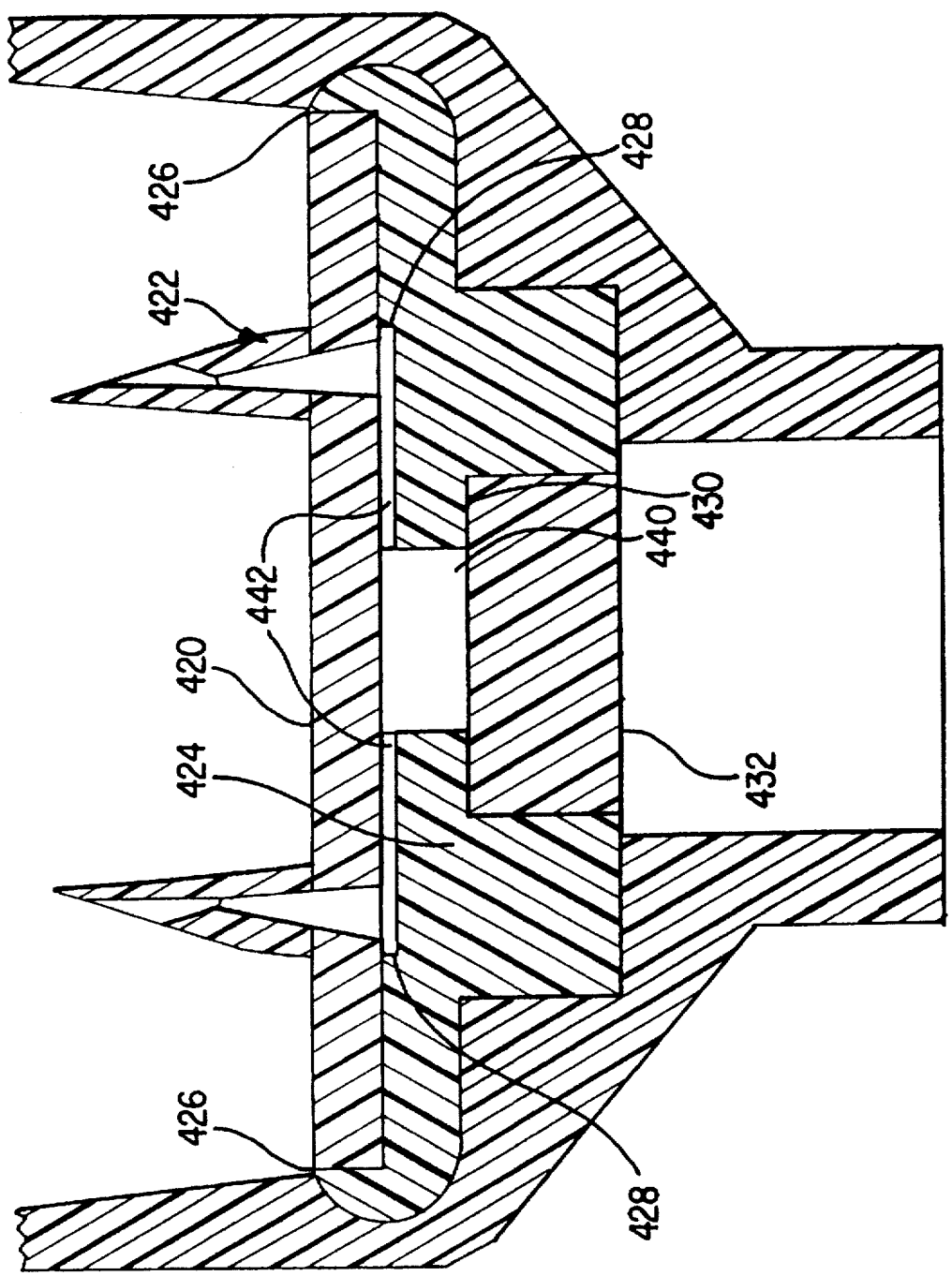

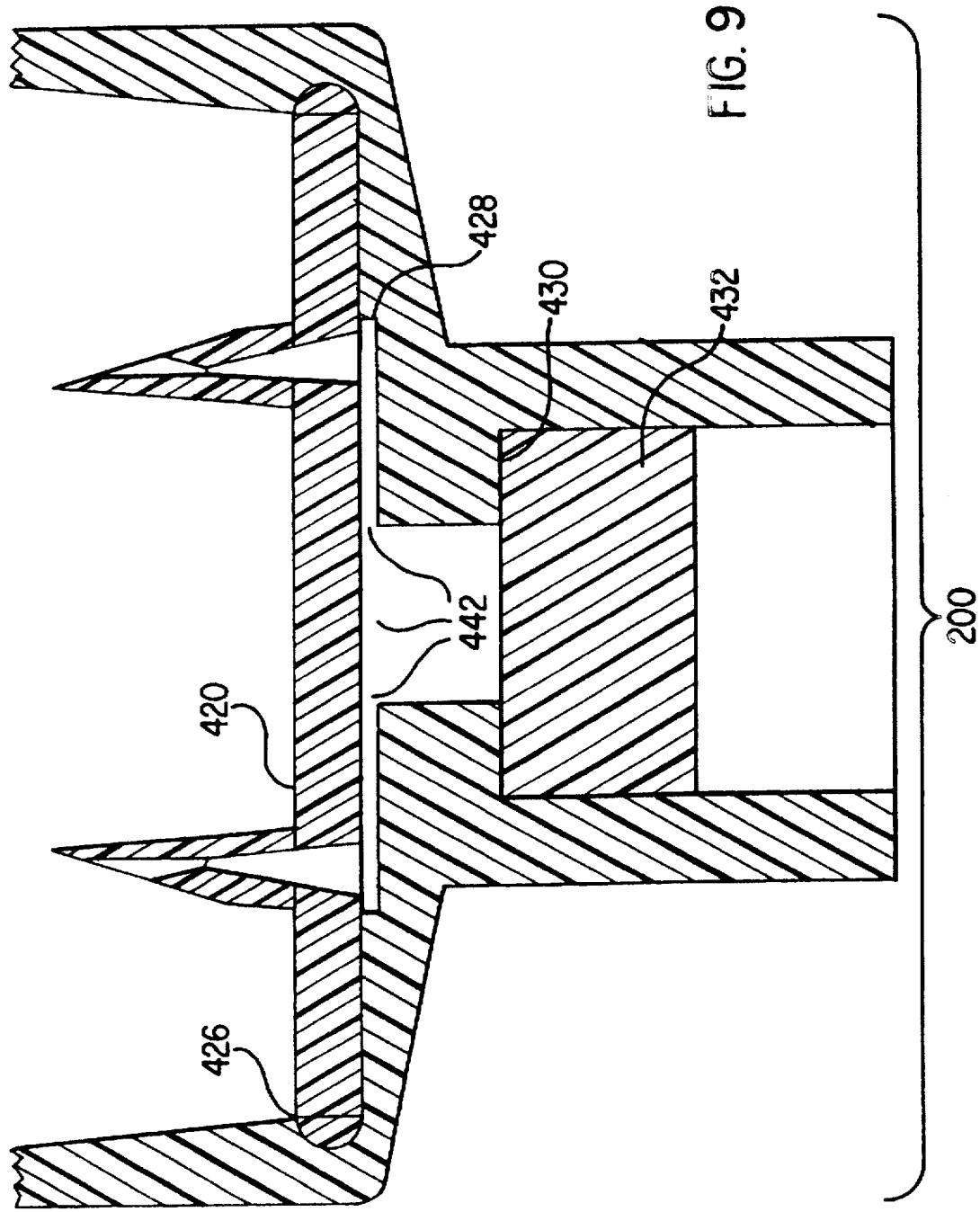

BLOOD COLLECTION DEVICE

Field of the invention

This invention relates to body fluid collection devices, particularly for the collection of whole blood. More particularly, the invention relates to fluid collection devices wherein multiple, individual, samples of fluid can be withdrawn simultaneously.

BACKGROUND OF INVENTION

The state-of-the-art in venous blood collection devices is the evacuated collection tube; a cylindrical, test-tube-like container, typically made of glass, that is evacuated and then sealed. The seal must be penetrable (that is, easily punctured by the cannula used to collect the sample) and be self-healing (to prevent contamination after filling). Most commonly, a thick rubber septum provides the seal, the thickness being required to ensure against loss of vacuum due to permeation of gas through the rubber(e.g., VACU-TAINERS® marketed by Becton Dickinson). Alternatively, the tube may be made of a biocompatible plastic and sealed with a multi-layer foil that carries a small, self-healing button of rubber on its outer surface (see, U.S. Pat. No. 5,033,476). The advantages of this latter embodiment are that (1) the plastic tube is lighter than glass, unbreakable, and easy to incinerate; (2) the vacuum-tight seal is easily made by an adhesive bond between the foil and the top surface of the plastic tube; and (3) the seal can be penetrated by a metal needle (or cannula) with a substantially reduced force.

Conventional evacuated tubes are very effective at collecting single samples of blood for clinical diagnostic purposes. The tubes can be made in a wide variety of sizes, each size being designed to collect a specific volume of blood (typically between 2 ml and 10 ml). Because the tubes are hermetically sealed, they can be charged with any one of a wide variety of chemical additives (such as anticoagulants) that are dictated by the specific analytical chemistry tests that are to be done on the sample. The primary disadvantage of this conventional type of blood collection device is that it yields only one blood sample for analysis.

Often the diagnostician wants several different types of tests done on a patient's blood: for example, cell count, clotting factor and serum-based chemistry tests may all be required. To meet this need, several blood samples must be collected, each with (or without) its own special chemical additive. With conventional technology, each type of blood sample is collected in a separate, evacuated collection tube. At other times, the entire test series may require only a single type of blood sample preparation (chemical additive), but the range of diagnostic tests requested cannot be done by just one diagnostic instrument. (A universal, fully comprehensive clinical chemistry diagnostic instrument does not yet exist in the marketplace.) In such cases, a separate evacuated tube may be used to collect a blood sample for each instrument; or a substantial volume of blood may be collected in a single collection tube, and then portions of this sample may be aliquoted into secondary containers, each portion being presented to a different diagnostic instrument to fulfill a portion of the test request. Conceptually, this aliquoting step can be avoided by shuttling the primary collection tube from instrument to instrument. However, there are limitations associated with the presentation of a single sample in its primary collection tube to a family of diagnostic instruments in series: (1) it takes more time to complete the full set of results than if the samples were analyzed in parallel, (2) a sophisticated sample transport mechanism and protocol (from instrument to instrument) is essential, and (3) the possibility of sample contamination increases greatly as the sample is shuttled from instrument to instrument and is introduced to a family of aspiration/ metering stations. The possibility of sample contamination is especially acute for tests that provide extremely high sensitivity or carry criminal sanctions, such as those for hormones and drugs. In such cases, a fresh sample that has not come in contact with any external surfaces (i.e., a sample that is free of "carry over" from other sample handling steps) is required.

Another disadvantage of conventional technology is the inconvenience of producing a pristine sample for archival purposes. Such archival samples must be prepared by aliquoting a portion of the collected sample into a secondary container, so that a portion can be stored for future reference. Finally, it is evident that the need to prepare multiple blood samples for analysis or archiving introduces an undesirable number of sample handling steps and disposables; and whenever aliquoting is involved there is the additional difficulty of maintaining positive patient identification.

Several attempts have been made to create a practical, manufacturable, multi-chambered blood collection device that permits the nearly simultaneous collection of several aliquots of blood.

U.S. Pat. No. 3,604,410 to Whitacre discloses a multi-tube blood sampler using two or more evacuated tubes which are closed by rubber stoppers. The evacuated tubes are fitted into a retainer with a needle partially inserted into the stopper. Subsequently, the cannula is inserted into the vein and the tubes are then pushed on the retainer so that the needle projects through the stoppers and into the tube cavity to permit the blood samples to be drawn. Whenever it is desirable to fill both tubes simultaneously, a pair of tubes may be carried on a common base. One disadvantage of this device is its cumbersome nature and the associated difficulty and expense of expanding the concept to more than two discrete chambers. Another disadvantage is that a special needle holder assembly must be manufactured for use with each combination of tube sizes.

U.S. Pat. No. 3,405,706 to Cinqualbre also discloses a multi-tube blood sampler. Although the orientation of the evacuated tubes relative to the needle is different from that described by Whitacre, the device is conceptually similar and thus suffers from similar drawbacks.

U.S. Pat. No. 4,166,450 to Abramson discloses a device for use with an intravenous needle for filling a single tube. However, the '450 patent does not suggest a means for preventing contamination if the device is used for multiple blood collections.

Thus, an object of the invention is to provide a single blood collection device for collecting a plurality of venous blood samples, each sample being of a distinct volume and reagent/chemical preparation, in a single blood collection step.

A further object of the invention is to provide a convenient way to collect and handle blood samples of relatively small volume (e.g., less than 500 µl each), thereby minimizing the amount of blood that must be withdrawn from a patient at any time (and thereby minimizing trauma).

An additional object of the invention is to provide a multi-chambered blood collection device as described above which requires no special handling and/or processing of the user and will thus readily conform to current practices for the collection and presentation of venous blood.

An additional object of the invention is to provide a multi-chambered blood collection device which meets diagnostician's need for a combination of discrete aliquots of patient's blood, each with its own special chemical treatment.

One additional object of the invention is to provide a multi-chambered blood collection device that provides a convenient way to collect and manipulate a plurality of samples of small volume (e.g., less than 500 μl each).

Further objects of the invention are to provide a multi-chambered blood collection device which is cost-effective, minimizes the number of disposables, preserves patient identification, and minimizes risk and/or exposure to health care workers through sample collection and/or handling and/or disposal.

In summary, the present invention overcomes the disadvantages of conventional blood collection devices by providing a means for collecting a plurality of blood samples, optionally each sample having its own chemical preparation or additive, with a single blood collection device in a single collection step. In addition, the device of the present invention is easy to manufacture and to use. Furthermore, the present invention is not limited to a particular geometric configuration and thus the device can be deployed in a variety of geometric shapes, allowing it to be easily interfaced with a variety of diagnostic instruments and metering systems.

DESCRIPTION OF THE FIGURES

FIG. 8 is a cross section view of a preferred alternate embodiment of the adapter assembly.

FIG. 9 is a cross section vies of an embodiment of a multi-piece adapter assembly

BRIEF SUMMARY OF THE INVENTION

Figure 1:
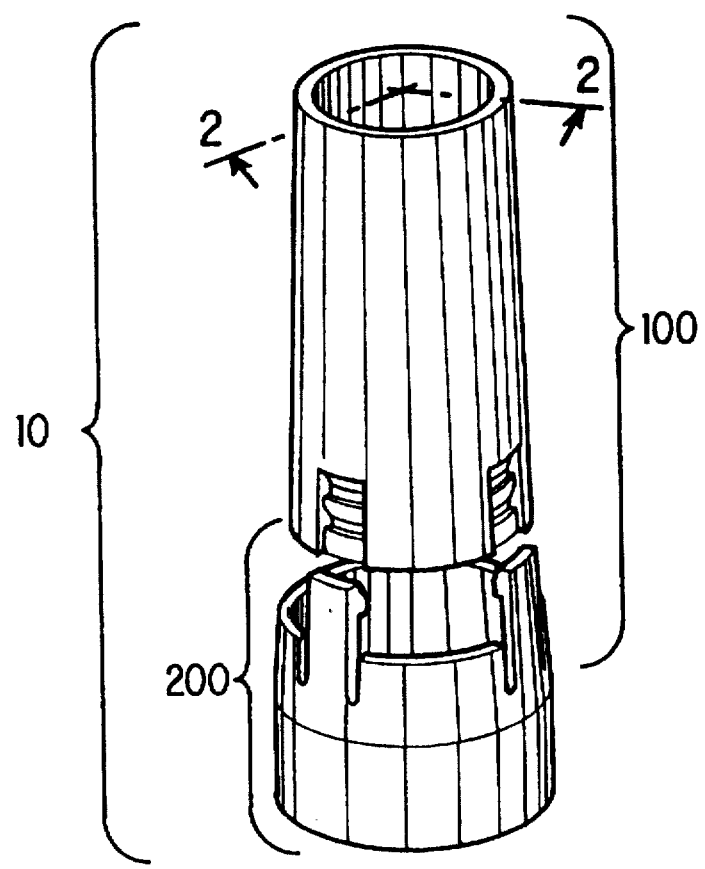
FIG. 1 shows a plan view of an embodiment of the invention.

Provided is a blood collection device comprising an adapter including a piercing probe, a manifold in fluid communication with the piercing probe, a plenum in fluid communication with the manifold, and having the plenum sealed with an adapter septum, and a collection device body having one or more evacuated chambers, the chambers having an aperture aligned with the piercing probe which is sealed with a septum. The adapter is movable relative to the body in such a way that the piercing probe may pass through the septum and fluidly connect the plenum with the evacuated chamber. In preferred embodiments, the adapter is releasably mounted to the body and the adapter, by the use of arms or prongs, slidingly engages with corresponding tracks or channels on the body.

Also disclosed is a device for transferring blood from a source to an evacuated chamber which comprises a piercing probe, a manifold in fluid communication with the piercing probe, a plenum in fluid communication with the manifold, and a septum which seals the plenum. Also provided is a method of transferring blood from a source to an evacuated chamber which utilizes this blood transfer device Additional disclosure is directed to a blood collection device comprising one or more asymmetric evacuated chamber, each chamber being sealed with a septum. In a preferred embodiment of this aspect of the invention, the device incorporates multiple asymmetric chambers which are sealed with a single septum.

DETAILED DESCRIPTION

As stated above, the present invention provides a blood collection device for collecting, and introducing in parallel, patient venous blood into a hermetically sealed multi-chambered evacuated vessel, while preventing cross-contamination between the evacuated chambers. Because each evacuated chamber is isolated from the others, each chamber may contain chemical reagents or additives which, in conventional evacuated tubes, would require separate tubes. The blood collection device of the invention allows simultaneous filing of each chamber by way of a distributor which can be selectively placed into essentially simultaneous fluid communication with a plurality of the evacuated chambers. The blood is then able to pass from the source through the distributor and into the chambers.

The device of the invention is easy to use as it is compact in shape and functions in a manner that closely resembles current blood collection technology. In particular, the blood collection device is designed for use with a conventional needle holder and thus may be used, when necessary or desired, in conjunction with conventional blood collection tubes for the collection of other blood samples. Thus, no special instructions, actuation devices, or dexterity are needed to employ the device. By collecting and containing all of the desired blood samples in a single multi-chambered vessel, the number of disposables is minimized and, because multiple tubes and secondary containers are eliminated, positive patient identification can be assured. Furthermore, as discussed in more detail below, the present invention employs features which make it straightforward and inexpensive to manufacture, despite the device's sophisticated capabilities.

The collection device may be manufactured as components and assembled just prior to the taking of the patient sample or, preferably, is pre-assembled and ready-to-use. The device can be manufactured by utilizing any number of methods known in the art, however, the preferred method is one in which most parts are injection molded of a suitable plastic. Such plastics make the device light, unbreakable, and manufacturable at a modest cost. Furthermore, the collection device is preferably made of a biocompatible, U.S. Food and Drug Administration (FDA) approved plastic, and metal components where desired, that is compatible with the blood samples, chemical treatments, and analytical tests to be done. Such materials are well-known in the industry (e.g., polyethylene teraphthalate, stainless steel).

The aperture of each collection chamber in the blood collection device as well as the distributor aperture is sealed with septums or self-healing seals after evacuation. Such seals and septums are known in the art and allow penetration by a point, i.e., needle, such that upon withdrawal of the point, the seal substantially reseals to preclude fluid passage. Suitable materials for the seals are well known in the art and should be selected based on the intended use for the device such as, biocompatibility, chemically inert and compatible with any chemical reagents or treatments contained therein, be FDA approved, and suitable for use in automated instruments. Each aperture may be individually sealed after evacuation. However, the preferred method of hermetically sealing the apertures of the chambers is with a single, continuous multilayer "foil" that is attached with a suitable adhesive to the surface of the vessel containing the apertures. Such methods are known in the art, see e.g., U.S. Pat. No. 5,033,476. Alternatively, the foil can be thermally bonded to the top surface of the collection vessel, either with or without an adhesive.

Briefly, the blood collection device includes a hermetically sealed multi-chamber evacuated body, wherein each chamber is hermetically sealed by a self-healing septum or seal. This septum is known in the art and allows penetration by a point such that upon withdrawal of the point, the seal substantially reseals to preclude fluid passage. An adapter is movably connected to the multi-chamber body and includes a plenum. The plenum is selectively movable relative to the evacuated chambers. The plenum includes a manifold which terminates at a piercing probe (one aligned with each evacuated chamber) at one end and a second penetrable septum or seal at the other end of the manifold. Because each chamber is individually sealed before and after blood collection, the chemical integrity of its contents is guaranteed. Thus, the device provides a means of collecting in parallel a plurality of blood samples, each with its own unique chemical treatment.

In operation, the blood collection device may be used with a needle holder assembly of conventional design in a manner superficially similar to the use of a conventional, evacuated blood collection tube (such as VACUTAINERS® marketed by Becton Dickinson). After the needle is inserted into a vein, the penetrable septum on the plenum is penetrated by the cannula, exposing the manifold to the blood source. Movement of the multi-chambered body relative to the adapter causes the piercing probe to pass through the septum and fluidly expose the manifold to the evacuated chambers. The vacuum in the chambers draws the blood through the cannula, the plenum/manifold, and the piercing probes, and into the respective chambers. When blood flow has ceased, the multi-chambered body/adapter unit may be removed from the needle holder assembly, as is the procedure with standard, evacuated collection tubes. The multi-chambered body may then be drawn away or removed completely from the adapter, allowing the self-healing septum to reseal, thereby providing a plurality of independent, sealed chambers containing blood.

General Features

FIG. 1 shows a plan view of an embodiment of the device of the invention having multiple chambers for blood collection. As shown in this figure, the device (10) comprises two main sub-components; the blood collection body (100) and an adapter (200). In this Figure the two components are shown in a "factory-assembled" configuration. As the device (10) is designed for use in commercial blood collection apparatus, the dimensions of the blood collection device (10) are preferably selected such that the exterior dimensions conform to those of commercial blood collection tubes.

Figure 2:
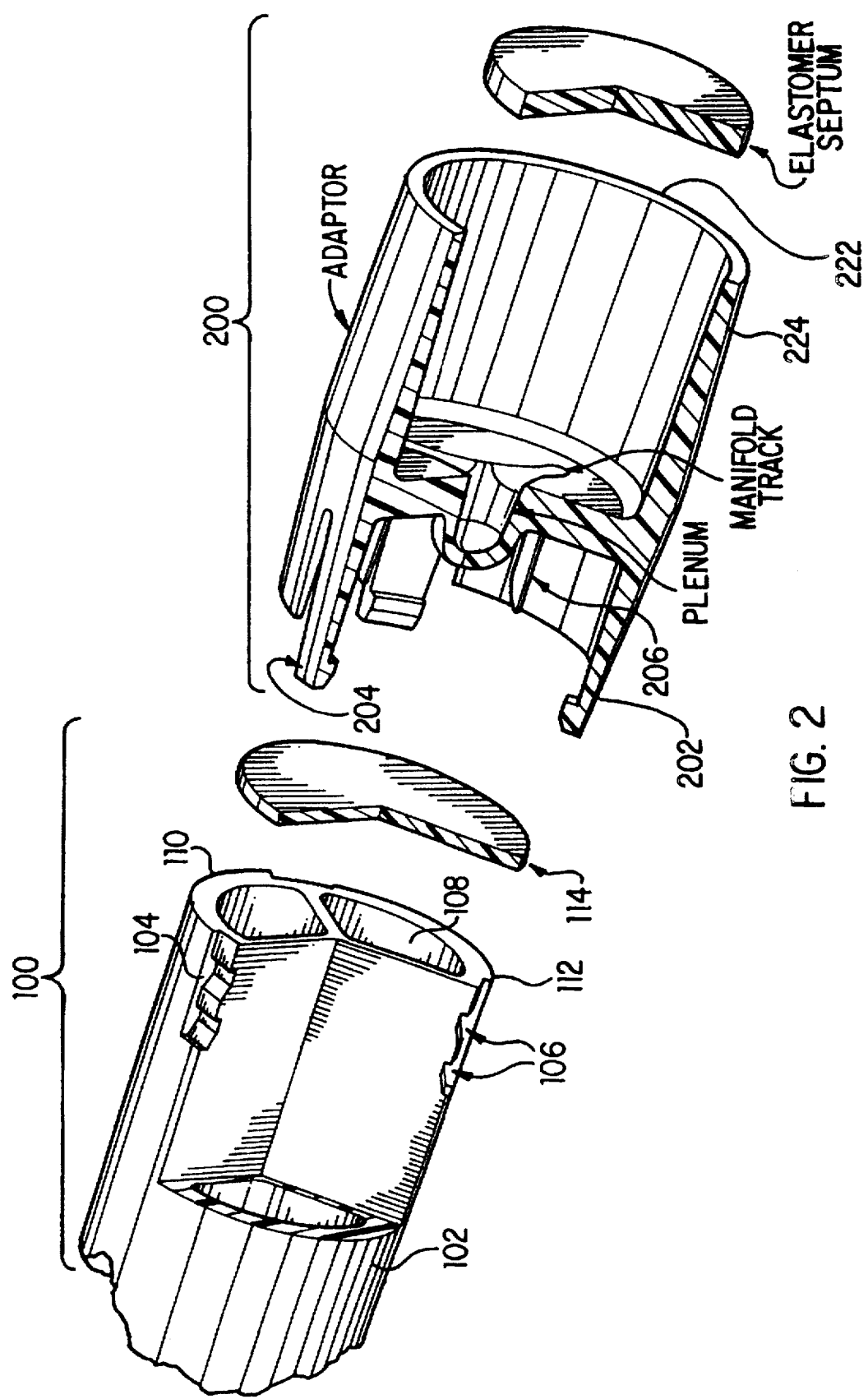
FIG. 2 shows a cutaway view of the embodiment of FIG. 1.

FIG. 2 shows a cutaway, disassembled, view of the embodiment shown in FIG. 1. The body (100) includes a sleeve (102) within which are located multiple collection chambers (110). Within the sleeve (102) the collection chambers (110) may be of any variety of lengths, keeping in mind the desirability of maintaining the dimensions of the device (10) which will lend itself to utilization with existing blood collection tubes. The length and number of chambers ultimately determine the volume of each chamber and this volume may be selected based on the amount of fluid which may be required for the intended use of the fluid. That portion of sleeve (102) not occupied by collection chambers (110) may be hollow as is preferred for ease of use and manufacturing. Collection chambers (110) are preferably molded within the sleeve and are each terminated by an aperture (108). The aperture (108) of each collection chamber (110) is sealed after evacuation by a self-healing septum (114) to ensure against vacuum and fluid leakage as is routine in existing blood collection devices. Optionally, the function of the septum may be accomplished by separate vacuum seals and fluid seals. In alternate embodiments, the far end (not shown) may also be manufactured to include an aperture therein and may optionally or alternatively include a handling means. When included, it is preferred that the handling means include an opening there through.

The near end (112) of the body (110) which mates with the adapter (200) includes one or more sliding joints (104) on the exterior surface. Each sliding joint (104) includes one or more, preferably two, detents (106). Sliding joints (104) are positioned to be slidingly engaged to corresponding snaps (204) which terminate from prongs (202) extending from adapter (200) such that when the prong (202) is mated in the sliding joint (104), each piercing probe (206) is aligned with a collection chamber (110). The near end (220) of adapter (200) includes an adapter sleeve (224) which can be mated to a conventional cannula via opening (222).

The piercing probes (206) are fluidly connected to the plenum (230) by manifold (232, only partially shown in this view). In a similar manner as described previously, plenum/manifold (230, 232) is sealed by a self-healing adapter septum (240) to ensure against vacuum and fluid leakage.

In general, the evacuated chamber will contain a chemical additive, preservative, reagent, etc. (such as heparin, sodium citrate, etc.) for addition to, or treatment of, the blood sample. The chemical may be placed in the chamber in either a liquid or solid form. It is important to rapidly disperse this chemical additive throughout the blood sample as soon as the blood flows into the chamber. If the diameter of the chamber is greater than about 7.5 mm, and the materials used for the manufacture of the internal chamber surfaces are reasonably wettable, e.g., a contact angle with the blood sample of less than about 75 degrees, then chemical dispersion can easily be achieved by gently rocking the tube back and forth from horizontal to vertical at least ten times by hand, which is common practice with conventional collection tubes. However, if the diameter of the evacuation chamber is smaller than that just described, as would be the case where it is sized to collect a blood volume of the order of 500 µl or less, surface tension tends to prevent the blood from displacing the air within the tube as the tube is rotated and thereby preventing convective mixing with any chemical additive. In this situation, wetability of the internal chamber surface is also a factor, as less wettable surfaces tend to inhibit liquid displacement. In those cases, solid mixing spheres made of a biocompatible material can be included inside the evacuated chamber. When the partially-filled chamber is inverted, the dense spheres will rapidly move by gravity to the other end of the chamber, thereby promoting fluid mixing.

Alternatively and preferably, the large resistance to fluid mixing in a small diameter tube or chamber (caused by surface tension) can be minimized by changing the shape of the chamber such that its cross-sectional dimensions are maximized within the geometric constraints of the device. Such cross-sectional dimensions can be empirically determined or, alternatively, can be predicted from a mathematical formula which predicts the cross-sectional dimension required for gravity (acting on the liquid) to completely overcome the liquid surface tension force as the chamber is manually rotated from the vertical to the horizontal position. For example, in the simple two-dimensional case of a chamber comprised of two parallel, horizontal plates, between which a liquid/air interface spans, the required plate separation distance (H) for gravity to completely overcome surface tension force is: $H=[(4 \sigma)(1 + \sin(\theta c))/(\rho g)]^{1/2}$, where $\sigma$ is the surface tension value of the liquid in air, $\theta c$ is the liquid contact angle with each plate, $\rho$ is the mass density of the liquid, and g is the acceleration of gravity. If the plates are separated by an amount H or greater, the liquid will detach from the upper plate and flow freely along the lower plate. If the separation distance is less than H, then some amount of agitation must be imparted on the chamber to initiate liquid flow. The person skilled in the art will recognize that the required cross-sectional dimension H for chamber geometries differing significantly from the preceding two-dimensional example will be larger than predicted by the foregoing equation. Similar methods have been utilized to accurately predict cross-sectional dimensions for embodiments of the present invention and the actual relationship can be determined by one skilled in the art from teachings in the art, or alternatively, the preceding equation can be used as a first-order approximation.

Figure 3:
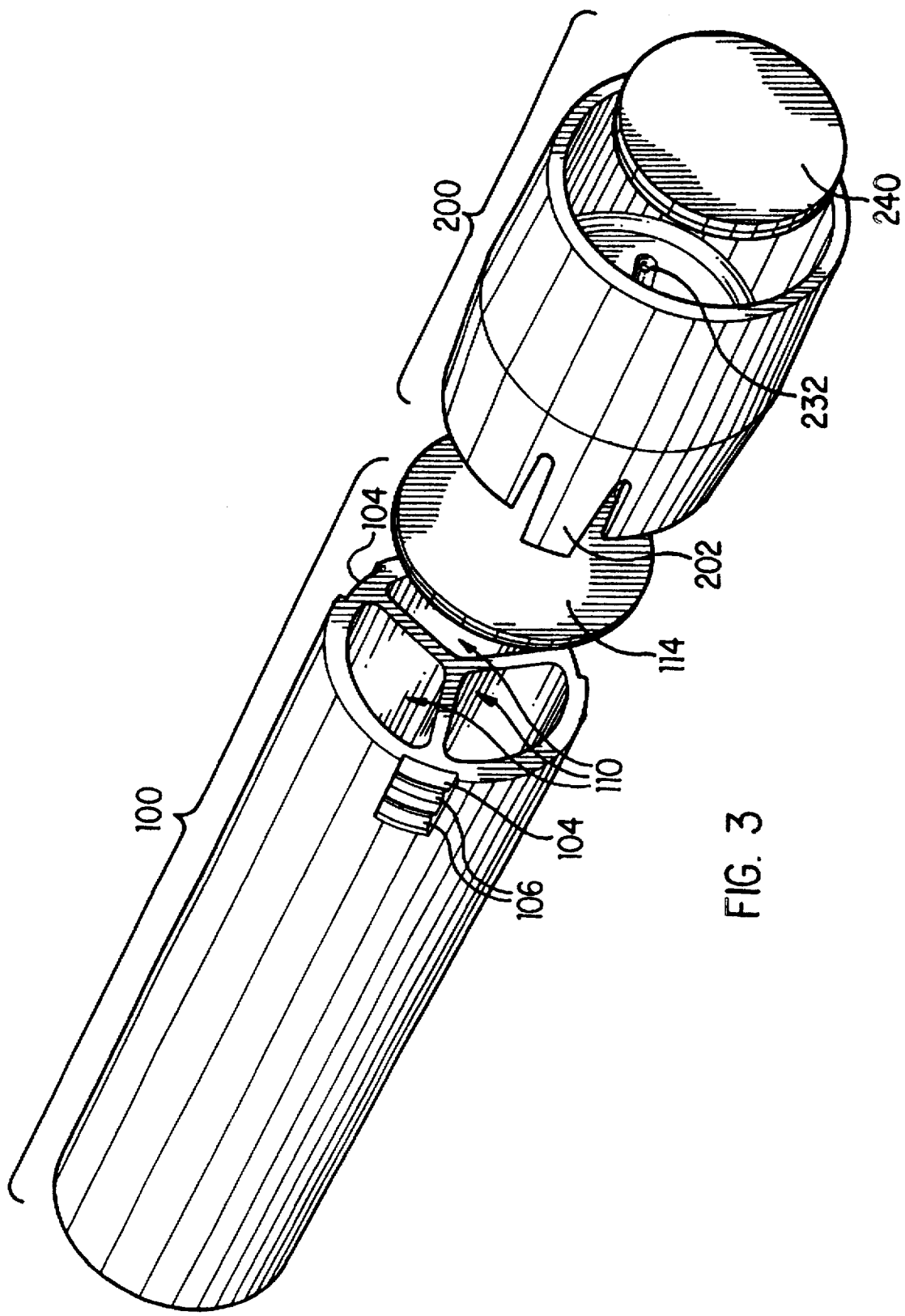
FIG. 3 shows a plan view of the embodiment of FIG. 1 in a disassembled form.
Figure 4:
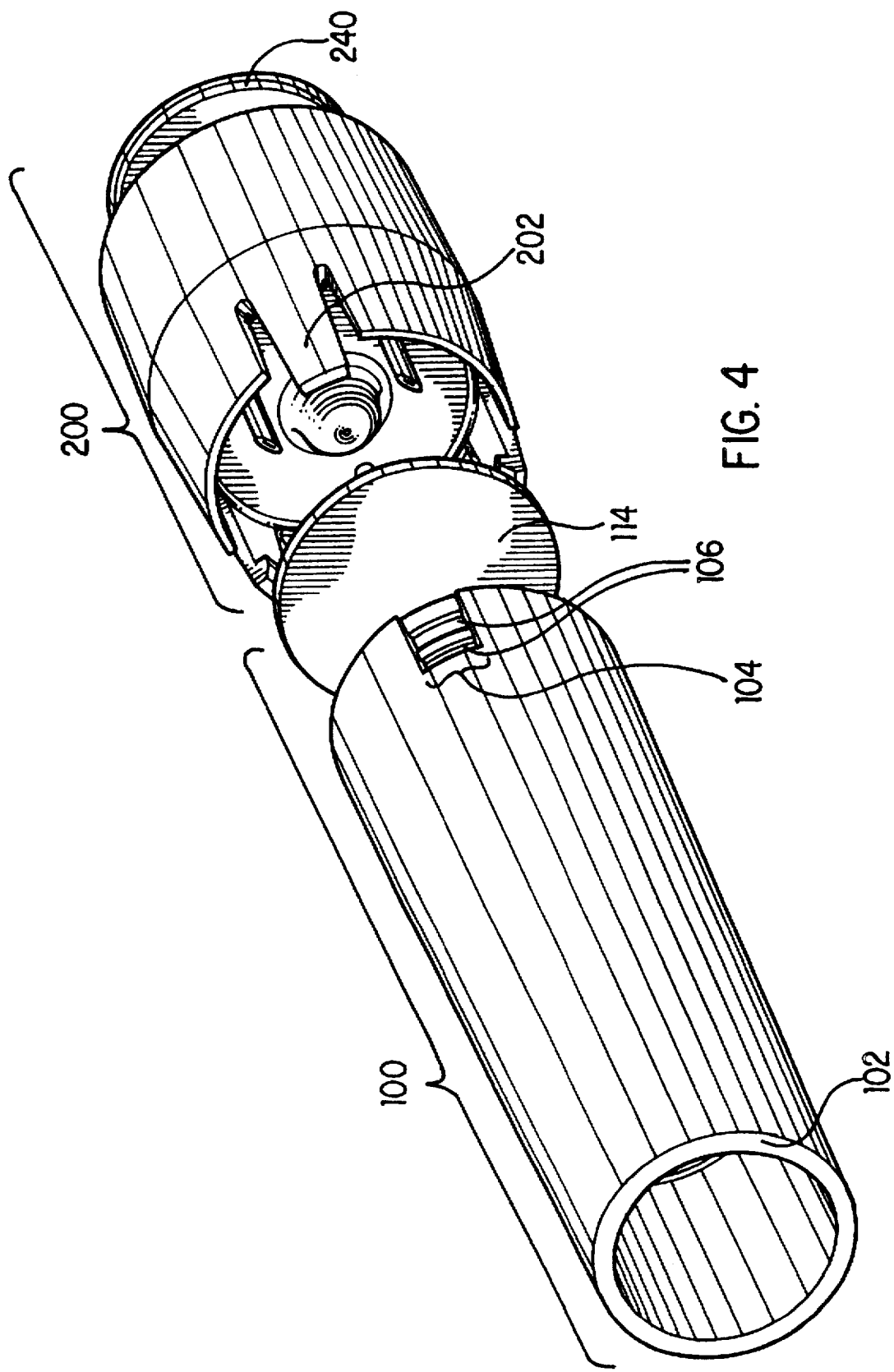
FIG. 4 shows an alternate plan view of the embodiment of FIG. 3.

Additional views of one embodiment of the invention are presented in FIGS. 3 and 4. These figures show a device of the invention in disassembled form and viewed from the near end (FIG. 3) and the far end (FIG. 4). Thus the major components of this embodiment shown in FIG. 3 include the body (100) showing three collection chambers (110) and a sliding joint (104), detents (106), and septum (114); adapter (200) showing prong (202) and a portion of the manifold (232) and adapter septum (240). FIG. 4 is an alternate view and shows body (100) including sleeve (102), sliding joint (104), detents (106), and septum (114); adapter (200) including prongs (202), snaps (204), piercing probes (206), exterior of plenum (230), and adapter septum (240).

Figure 5:
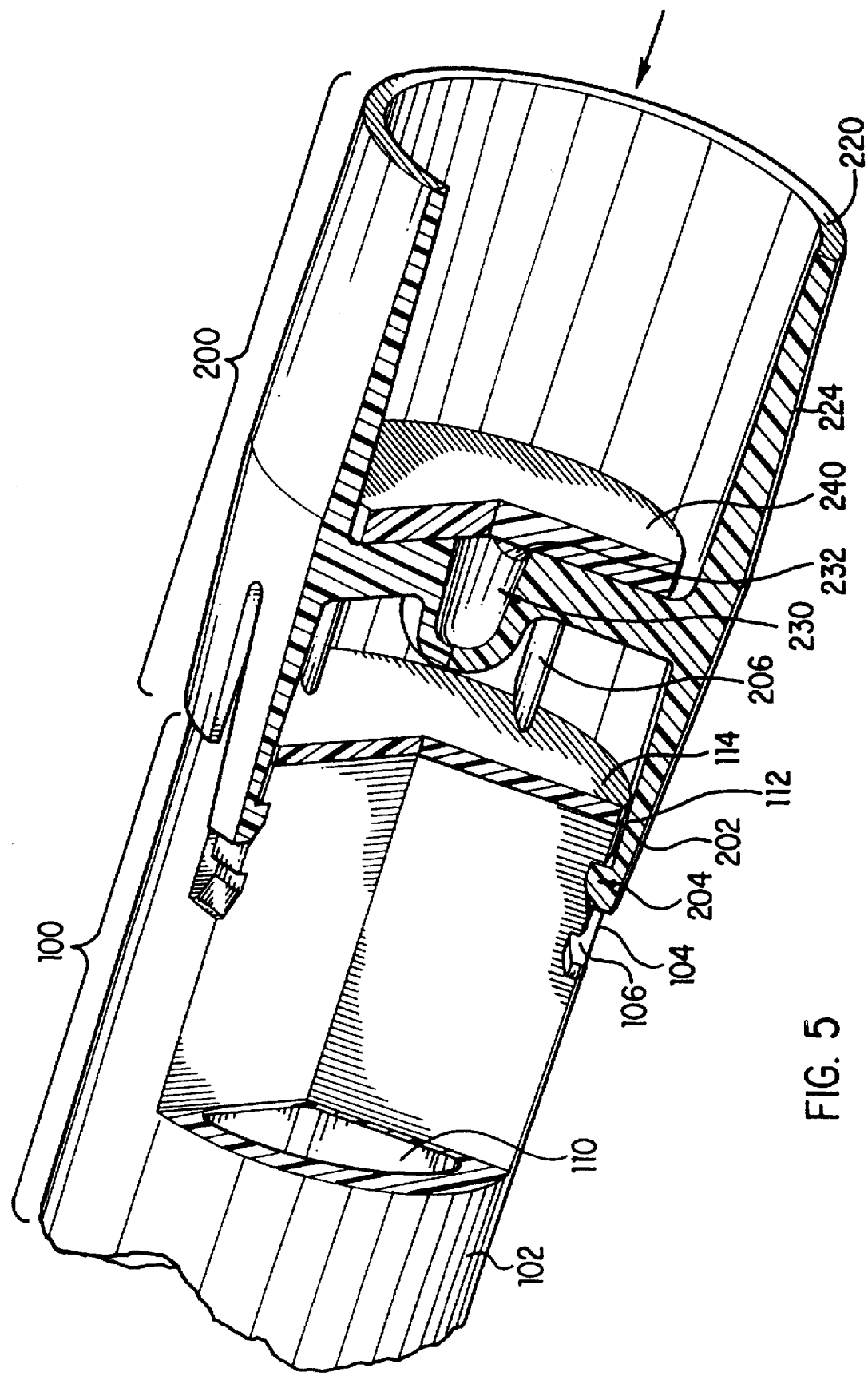
FIG. 5 is a cross section view of the plan view of FIG. 3.

FIG. 5 shows a cutaway view of the device as it is assembled prior to use. As can be seen by reference to this figure, the terminating button (204) of prong (202) which extends from the adapter (200) has engaged the first of two detents (106). Piercing probes (206) are thereby in position to penetrate septum (114) and are aligned with chamber aperture (108; not shown). As shown in this view, adapter septum (240) provides a vacuum tight seal for plenum (230).

Figure 6A:
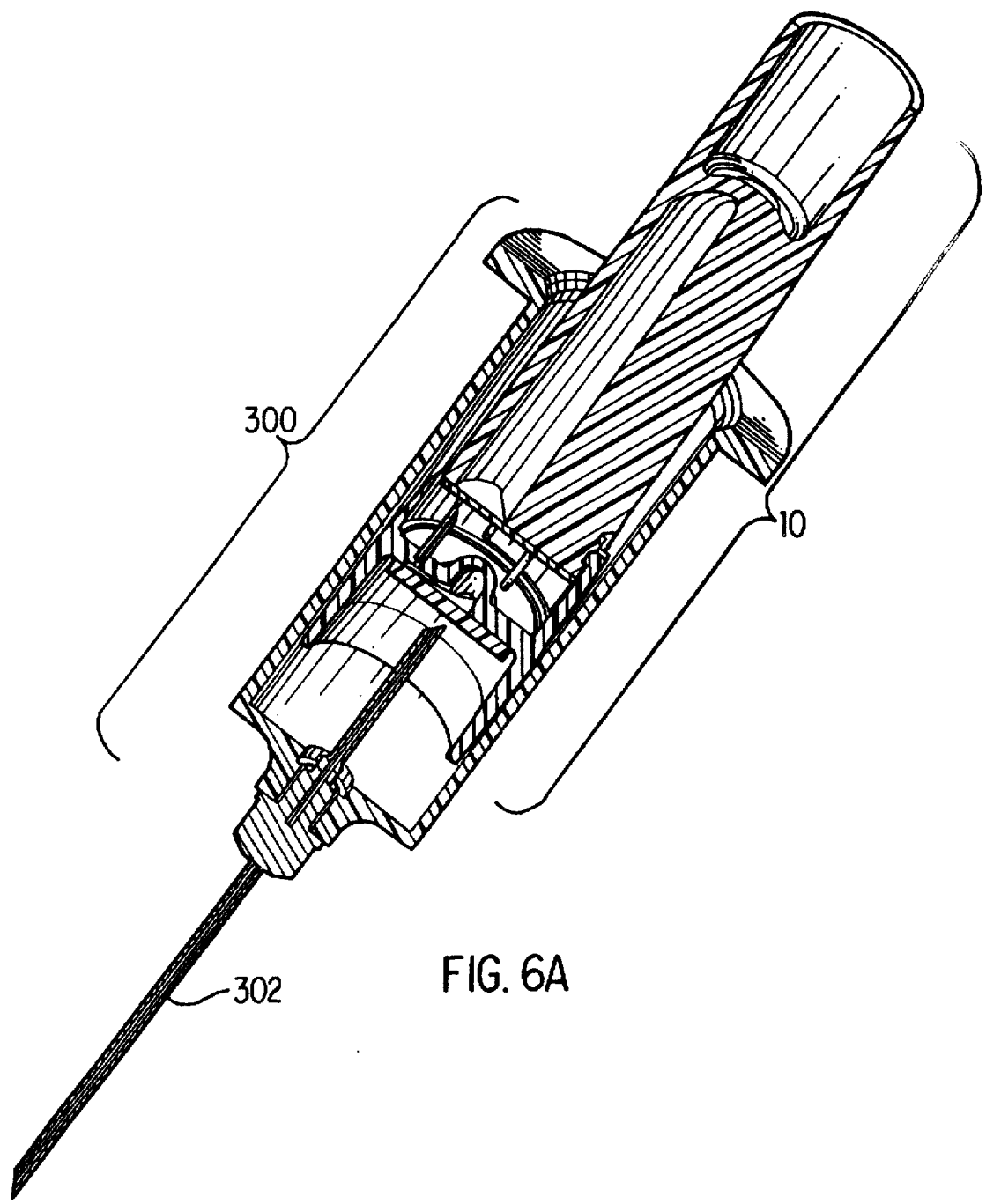
FIGS. 6a through 6c show the operation of an embodiment of the blood collection device of the invention.
Figure 6B:
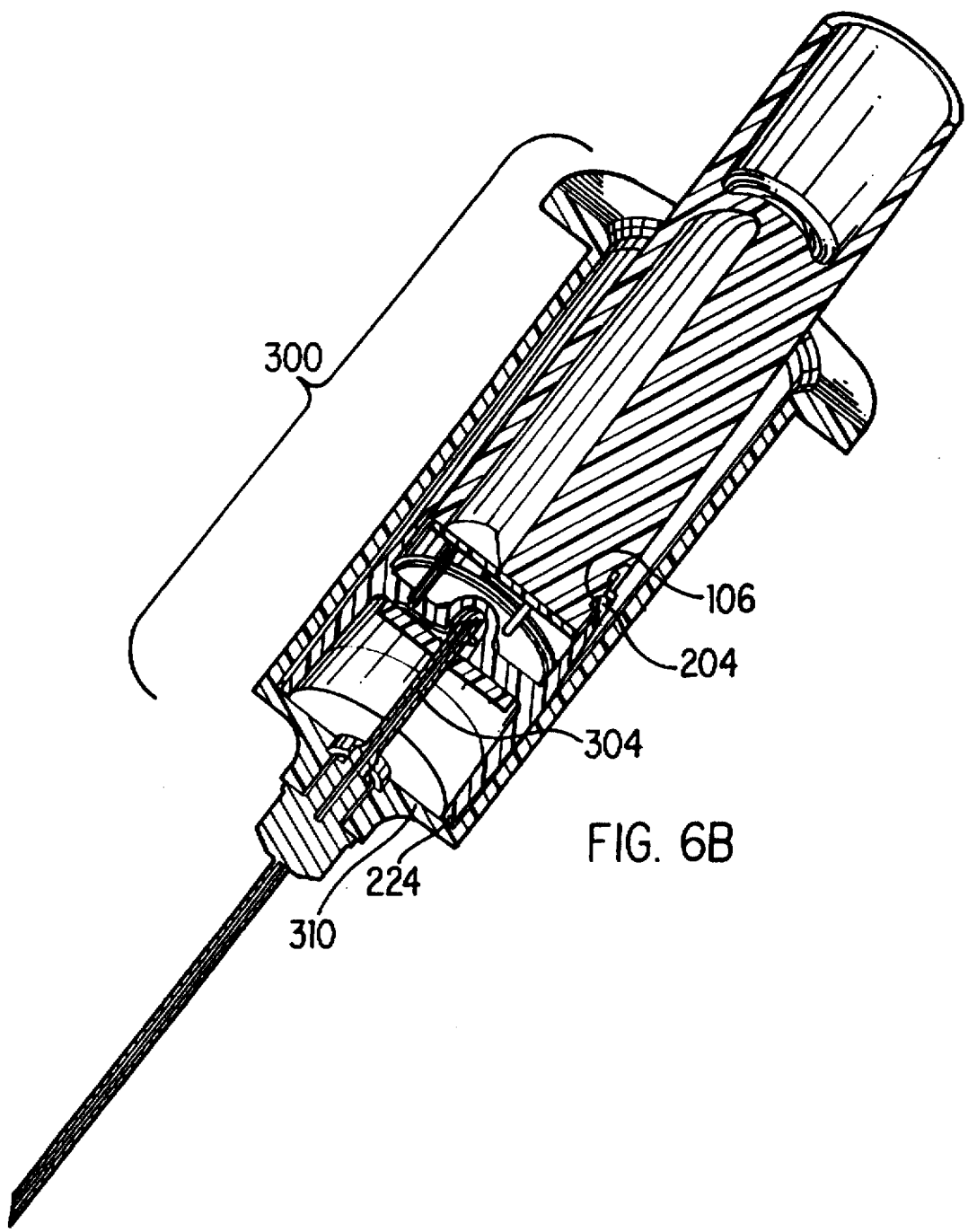
Figure 6C:
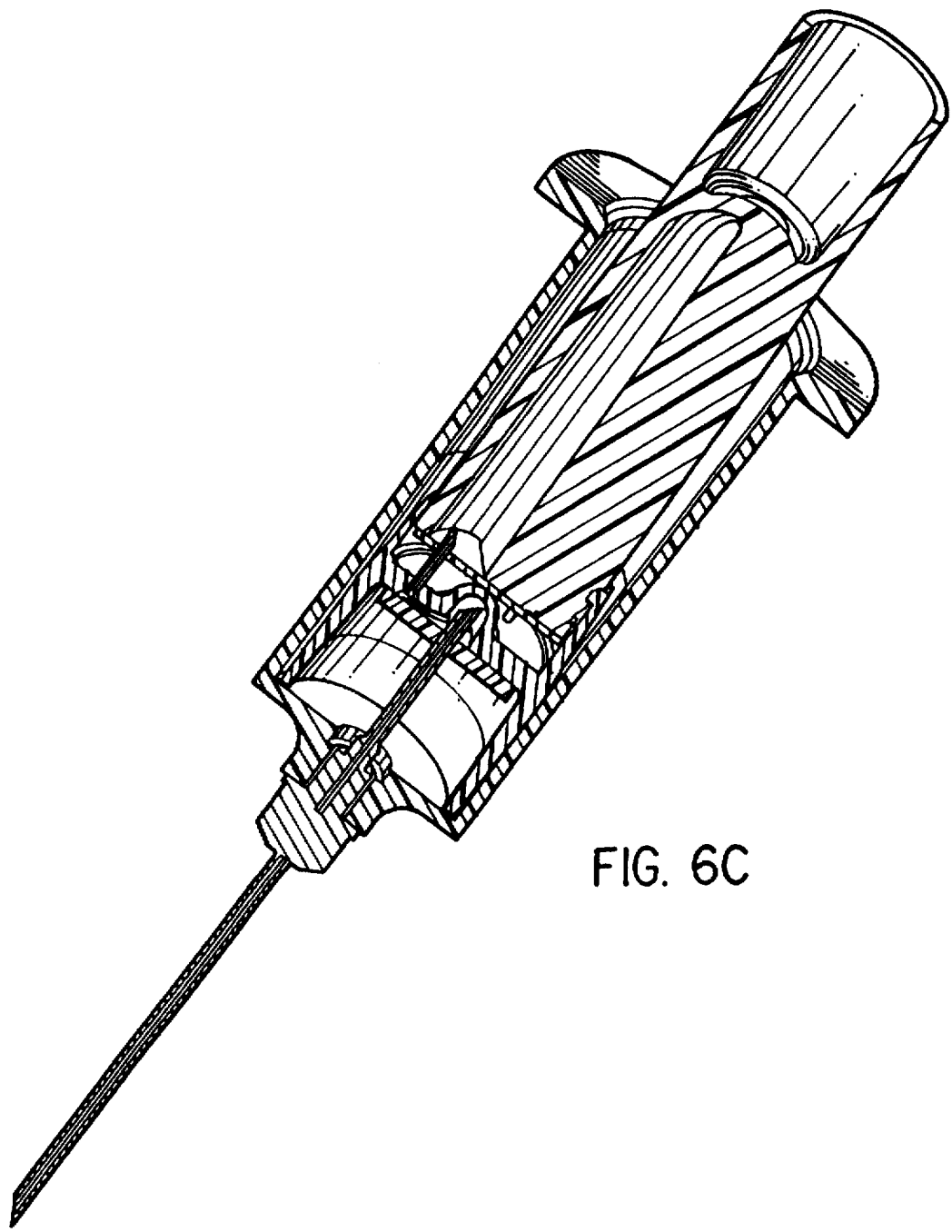

The operational sequence for blood collection with this device is illustrated in FIGS. 6a through 6c. Briefly, these figures show the orientation of the device when it is first inserted into the prior art needle holder before venapuncture (FIG. 6a); its position after partial insertion (with the arrow indicating application of pressure on the device), when the cannula has pierced the adapter septum into the plenum (FIG. 6b); and finally its position after full insertion of the blood collection body into the adapter, with the piercing probes fully entered into the evacuated chambers to expose the entire flow path to the internal vacuum for blood draw from the patient's vein (FIG. 6c).

As shown in FIG. 6a, the blood collection device (10) is inserted into a conventional needle holder assembly (300), as would be done with any conventional evacuated collection tube, and the needle (302) is inserted into the patient's vein (not shown). In FIG. 6b, pressure is applied to the device (10) causing the adapter septum (240) which overlies the plenum/distributor (230/232) to be penetrated by the cannula, thereby exposing the plenum and manifold to the blood source. At this stage of operation, snaps (204) have slidingly abutted and engaged the first of the detents (106). In addition, the end face of adapter sleeve (224) now abuts the inner face of the floor of the needle holder assembly (310). As additional insertion force is applied to the blood collection device (10), see FIG. 6c, the yield force of snap (204) and detent (106) is overcome and the body (100) moves relative to the adapter (200), causing the piercing probe (206) to pass through septum (114) and fluidly expose the manifold (232) to the evacuated chamber (110). The vacuum in the chamber draws the blood through the cannula (302), the plenum (230), manifold (232), piercing probe (206), and into the chamber (110). When blood flow has ceased, the blood collection device is removed from the needle holder assembly and the adapter septum self-heals to provide a fluid-tight seal within the blood collection device, as is the procedure with conventional collection tubes.

Figure 7:
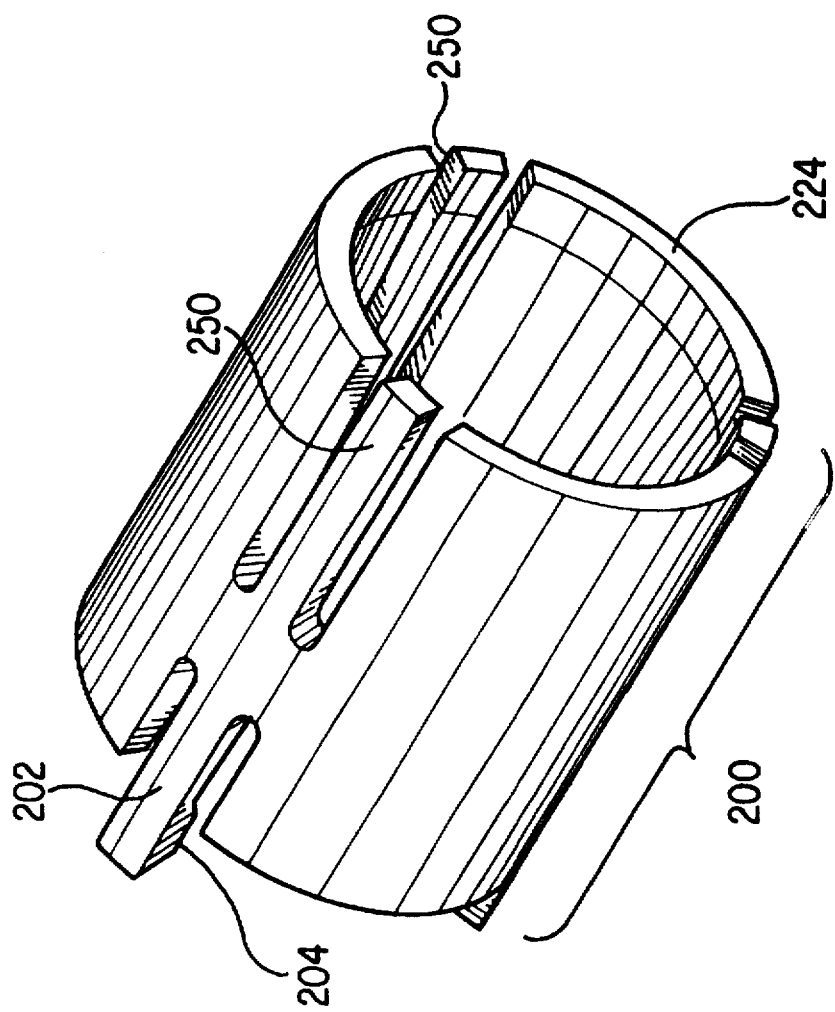
FIG. 7 is a cross section view of an alternate embodiment of the adapter assembly.

As shown in FIG. 7, an optional feature of the adapter includes means for detaching the adapter from the collection vessel. One such means is provided by lever (250, two of three shown in this view) molded into the adapter sleeve (224). The lever (250) is aligned with prong (202) such that by pressing inward on the lever, prong (202) is cantilevered away from the chamber (not shown), allowing the snap (204) to clear its corresponding detent and the adapter to be removed from the body. Other such means, e.g., incorporating break-away prongs, will be readily apparent to those skilled in the art. Thus, this optional feature provides a collection vessel containing the blood sample for further processing, e.g., presentation to a diagnostic instrument.

The order of events described above are not critical to the functioning of the device. For example, as long as the plenum/manifold assembly is leak-tight, the device will function equally well if the piercing probe on the adapter penetrates the plenum of the collection body before the cannula has the opportunity to penetrate the adapter septum. Furthermore, while it is preferred that the device be configured such that the adapter sleeve "bottom out" in the needle holder just as or immediately after the cannula penetrates the adapter septum, such is not necessary for the functioning of the device of the invention. In a similar manner, it is not necessary that the body be configured with a sliding joint having two detents. Thus, alternate embodiments for engaging the body and the adapter are readily apparent, e.g., a "one-step" insertion is contemplated where no additional force is needed to overcome the yield force of the first engagement of the snap/detent sliding joint.

As stated above, a preferred embodiment has the adapter sleeve "bottoming out" against the bottom surface of the conventional needle holder after the cannula pierces the adapter septum, and to initiate blood flow, an additional insertion force is applied to the collection body to overcome the yield force of the first engagement of the snap/detent slidable joint, with the adapter held in place by the needle holder body. Alternatively, the device can be designed such that the cannula "bottoms out" against the inside surface of the plenum before the adapter reaches the bottom of the needle holder. If this alternate configuration is employed, the materials employed in the manufacture of the distributor assembly must be of sufficient strength to resist the force applied by the cannula as the collection body is pushed down onto the piercing probe(s). However, this configuration is less preferred since the tip of the cannula needle may be bent by, or buried in, the inside surface of the plenum and restrictions to blood flow may result.

The Multi-Chamber Device

The preferred embodiment of the present invention consists of a single blood collection body having at least three separate blood collection chambers, each with its own chemical additive and volumetric capacity, as required by a particular testing procedure. Because the piercing probes must align with the apertures of the chambers in the collection body, the adapter must be keyed for proper orientation during assembly. In FIGS. 1 through 5, a device having three chambers is shown. In this particular embodiment sliding joints (104) and detents (106) on the body (100) align with prongs (202) and snaps (204) on the adapter (200). Preferable, detent (106) is designed to engage a snap of particular configuration, e.g., a cantilever snap. In a similar manner, sliding joint (104) is preferably designed of dimensions to ensure a snug fit with prong (202). A further alternate means assures alignment for shipping of the device by providing a track, for instance an angled, e.g., 'L' or 'Z', shaped groove cut into the body, designed to mate the adapter prongs to the body. This configuration allows for a "locked" shipping position, with a slight turn of the adapter relative to the body readying the device for use. Other variations to achieve alignment will be readily apparent to those skilled in the art. Since it is important that when a multi-chambered device of the invention is employed, the body and adapter fit together in only way, i.e., a piercing probe aligned with a chamber aperture, one can employ, for example, keyways, splines, or non-symmetric shaping of mating surfaces to achieve proper engagement and alignment. These engagement means should be designed to ensure not only proper alignment but also a snug, solid feel to the device during use.

As stated above, the evacuated chambers must be provided with a seal or septum which provides a vacuum as well as a fluid tight seal. Preferably, the seal is sturdy, biocompatible, and highly impermeable to gas so that it can retain the vacuum conditions within each chamber over an extended shelf life. In addition, the seal should be compatible with all the chemical additives that may be used to prepare the blood sample for analysis (e.g., heparin, sodium citrate, etc.). Conventional and well known multilayer foil seals are preferred as they have proven to be very effective for sealing single-sample, plastic evacuated tubes for blood collection. In the multi-chamber device of the invention, it is also preferred that a single multilayer foil seal (as compared to the use of individual seals for each chamber) be used. The use of a single foil strip to simultaneously seal all chambers simplifies the manufacture of the body, provides assurance that all samples will be contained in the body, and permits the use of plastic piercing probes on the adapter.

Preferably, the foil seal carries a layer of self-healing polymer on its top surface (opposite to the surface adhesively bound to the body). One purpose of this self-healing polymer is to provide an adequate air- and liquid-tight seal when the foil is penetrated by the probes on the adapter during blood collection. When the probes pierce the foil seal and expose the manifold to the vacuum inside chambers, blood flow is initiated from the patient, through the needle, plenum and into the chambers (see FIG. 6). When filling is complete and the probes are retracted from the chambers, this polymer must reseal so that the blood in each chamber remains confined and isolated from the other chambers as well as the exterior of the body.

Optionally, the surface area of the body available for bonding of the foil may be provided with surface texture or raised features, on the order of 0.013 to 0.025 cm high, around all apertures as well as the outer rim of the body. These raised features enhance the sealing process to ensure a continuous seal at all key regions of the sealing surface.

Adapter

In the preferred embodiment, the adapter is injection molded with the piercing probes insert molded in the adapter following techniques well known in the art. In this process, the piercing probes are placed into the tool just prior to molding of the part and ensures an air tight seal at the juncture of the manifold and the piercing probe. Alternatively, the probes may be press-fit into holes in the distributor after molding of the part. The probes are preferably standard gauge stainless steel needles.

While a one-piece molded adapter as shown in FIGS. 1 through 7 is preferred, other alternate configurations may be used. A detail of one such embodiment of the adapter is shown in FIG. 8. This embodiment utilizes two manufactured components and a self-healing septum. The orifice plate (420) is disc-shaped (in top view) and can be injection-molded with penetrating probes (422) integral to the mold and protruding from the upper surface (i.e., the surface to be mated with the body). A manifold insert (424) can also be injection-molded and is generally doughnut-shaped (again, in top view) as with the orifice plate (420). The manifold insert (424) has an insert recess (426) to receive the orifice (420). In addition, the insert (424) provides channel recesses (428) and a septum recess (430) to receive the septum (432). The dimensions of the septum (432), orifice plate (420) and manifold insert (424) are such that a plenum (440) is created. In addition, when orifice plate (420) and manifold insert (424) are abutted, channel recess (428) allows for the formation of a manifold (442) for fluid flow between plenum (440) and penetrating probes (422).

The external dimension of the insert recess (426) is sized such that an interference fit can be created between it and the outer circumference of the orifice plate (420), thereby creating a fluid-tight seal between the manifold insert (424) and the orifice (420) that prevents any leakage of air or blood during sample collection. Channels recesses (428) are included as a further recess on the mating surface of the insert (424). Thus, when the orifice plate (420) and manifold insert (424) are mated, a manifold (442) is created between the two pieces. The manifold (442) fluidly connects the penetrating probes (422) to the plenum (440) which receives the blood from the cannula. In further optional modifications (not shown), the manifold can be contorted to increase the path length and thus the resistance to blood flow in order to independently adjust the filling times of the various chambers in the collection vessel or body. This may be particularly appropriate if the chamber volumes differ significantly.

The primary concern during blood collection is that the adapter not leak blood to the surroundings or leak air from the surroundings into the chambers (thereby losing precious vacuum) during blood collection. A secondary concern, when the two piece adapter is utilized, is the leakage of blood out of the manifold and into the gap between the orifice and manifold insert. Among other things, if severe enough, such leakage might create a short circuit that will direct flow preferentially to one chamber over another, thereby affecting their relative fill rates. Such leakage can be prevented by using an adhesive on the sealing surface between the parts of the adapter. Alternatively, a slight surface elevation or step can be included on the boundaries of the manifold. These raised surfaces can be employed as concentrators for sealing with adhesive or for ultrasonic welding, or alternatively, they can be mated to recesses in the orifice plate carrying the penetrating probes.

As conceived in FIG. 8, the assembled, orifice-manifold insert is snapped into a recess in the inner wall of the adapter to rigidly fix it in place. Because the penetrating probes must align with the apertures of the chambers in the collection body, the adapter, orifice-manifold insert assembly and body must be keyed for proper orientation during assembly as discussed previously. Also, of course, the surfaces on the adapter that receive the orifice-manifold insert assembly must be appropriately scaled to the size of the needle holder assembly and length of the cannula so that the adapter assembly shown in FIG. 8 will lead to the full penetration of the septum by the cannula when the device is inserted into a needle holder during blood collection.

A more preferable design for a multi-piece adapter assembly is shown in FIG. 9. In this alternative design, the details of the manifold insert (424 in FIG. 8) described above have been incorporated into a single molded piece, thereby eliminating one assembly step. Thus features of the prior embodiment, such as channel recess (428) and septum recess (430), which are necessary to provide the void volume of manifold (442), are instead designed as part of the adapter housing which results upon insertion of orifice plate (420). In this alternative design, the recess (426) on the adapter that receives the disc-shaped, orifice plate (420) must be carefully sized to provide an interference fit that prevents any leakage of air or blood during blood collection. In order to assure an especially tight fit between the adapter and orifice, a further adaptation is to mold the orifice plate in a slight concave shape (convex on the penetrating probe side of the disc), so that when the orifice plate is snapped into place in the adapter base, there are additional lateral forces acting along the contact surface.

Penetrating Probes

As previously disclosed, in the preferred embodiment the piercing or penetrating probes are of a biocompatible, U.S. Food and Drug Administration (FDA) approved metal compatible with the blood samples, chemical treatments, and analytical tests to be done. Standard gauge stainless steel needles are preferred.

In some embodiments, the penetrating probes may be injection-molded as part of the orifice plate as shown in FIGS. 8 and 9. It is highly desirable for the penetrating probe to shear the self-healing polymer:foil seal on the collection body without coring out a segment of the polymer, because the cored piece may get lodged inside the probe and block the blood flow. In addition, coring may leave a path for fluid leakage upon removal of the probe after blood collection. To minimize the possibility of coring several techniques can be employed. The septum can be manufactured to have a narrowed thickness at the place of penetration. Alternatively, the heal of the needle may be slightly dulled. Still further, to retain a plastic tip of extreme sharpness, an asymmetric probe shape is devised with its opening along the plane of shear. The complex internal orifice geometry of such a probe (1) permits a relatively large pathway for blood flow while minimizing external probe diameter and (2) simplifies the mold design because there are no undercuts to contend with during the ejection of the part from the mold. Also, the external surface of the probe is tapered so that when the probe is inserted into the polymer:foil composite seal, to expose the probes to the evacuated chambers and initiate blood flow, the polymer will be progressively compressed around the probe to create a seal that will contain the vacuum as well as the blood that flows into the chambers in the collection vessel. To further improve the seal between the distributor and the polymer:foil seal on the collection body, raised surfaces or ridges can be added to the probe-side surface of the orifice plate to locally compress the polymer and create a seal. Naturally, to contain both vacuum and liquid, these raised surfaces must be contiguous and completely surround the base of each probe and/or the circumference of the orifice plate.

Additional Features of the Devices

As stated above, the height, width, and number of prongs/sliding joints combine with the polymer's elastic modulus to determine the total force needed to cause the blood collection body to slide toward the adapter and the piercing probes. Ideally, these parameters should be adjusted so that the force required by the phlebotomist closely matches that required for a cannula to penetrate a standard septum (on the order of 3 lbs. of force or less). In this way, the "feel" of the device will be very similar to the conventional Vacutainer during blood collection.

Optionally, the device may incorporate a disc-shaped base on the far end of the device that is larger in diameter than the body. Such a feature may be useful for mechanical or robotic manipulation of the device after blood collection. For example, after blood collection the adapter must be removed to access the blood in the collection chambers. The removal of the adapter from the body may be done electromechanically by placing the device in a holder which firmly grasps the body at its base so that adequate force may be applied to detach the adapter. A similar lip, or other feature for mechanical manipulation, can be added to the narrow end of the adapter to facilitate the grasping and removal of the adapter from the vessel. Alternatively, the adapter can be pushed off by a rod that is articulated upward through a guide hole (not shown) in the center of the body while the body is anchored to the adapter. A further, alternative, means for withdrawing the collected blood includes penetrable ports or seals in the adapter and aligned with the chambers, or penetrable ports or seals at the far end of the device, which allow the collected blood to be removed or withdrawn from the chamber without removal of the adapter.

The present invention has been described with reference to preferred embodiments. One of skill in the art will readily appreciate that changes, alterations or modifications can be made to these embodiments without departing from the true scope and spirit of the invention.

We claim:

1. A blood collection device, comprising:
   (a) an adapter including a piercing probe, a manifold in fluid communication with the piercing probe, a plenum in fluid communication with the manifold, the plenum sealed with an adapter septum; and
   (b) a body having one or more evacuated chambers, each of said chambers having an aperture aligned with the piercing probe, each of said apertures sealed with a septum;
   the adapter selectively movable relative to the body to pass the piercing probe through the septum and fluidly connect the plenum with the one or more evacuated chambers.

2. The blood collection device of claim 1, wherein the adapter is releasably mounted to the body.

3. The blood collection device of claim 1, further comprising a needle holder assembly for cooperating with the adapter and body.

4. The blood collection device of claim 1 wherein the body includes means for slidingly engaging the adapter.

5. The blood collection device of claim 1 comprising a plurality of chambers.

6. The blood collection device of claim 5 wherein a single septum seals the plurality of apertures.

7. The device of claim 1 further comprising means for immobilizing the adapter relative to the body for shipping.

8. A device for transferring blood from a source to an evacuated chamber, comprising:

a piercing probe, a manifold in fluid communication with the piercing probe, a plenum in fluid communication with the manifold, and a septum which seals the plenum.

9. A method of transferring blood from a source to an evacuated chamber, comprising:

(a) providing a blood transfer device comprising a piercing probe, a manifold in fluid communication with the piercing probe, and a septum which seals the manifold;

(b) penetrating the septum on the manifold to expose the piercing probe to the blood source; and (c) passing the piercing probe through a second septum to fluidly connect the piercing probe to the evacuated chamber.

10. A blood collection device, comprising:

(a) one or more evacuated chambers, wherein in each of said one or more evacuated chambers the cross-section perpendicular to the long axis is asymmetric in shape, each of said one or more evacuated chambers having an aperture; and (b) a septum which seals each aperture.

11. The blood collection of device of claim 10 comprising a plurality of evacuated chambers.

12. The blood collection device of claim 11 wherein each chamber is sealed with a septum.

13. The blood collection device of claim 11 wherein a single septum seals a plurality of apertures.

* * * * *